United States Patent [19]
Poirier

[11] Patent Number: 5,935,781
[45] Date of Patent: Aug. 10, 1999

[54] APOLIPOPROTEIN E POLYMORPHISM AND TREATMENT OF ALZHEIMER'S DISEASE

[75] Inventor: Judes Poirier, Boisbriand, Canada

[73] Assignee: McGill University, Montreal, Canada

[21] Appl. No.: 08/727,637

[22] PCT Filed: Apr. 26, 1995

[86] PCT No.: PCT/CA95/00240

§ 371 Date: Feb. 21, 1997

§ 102(e) Date: Feb. 21, 1997

[87] PCT Pub. No.: WO95/29257

PCT Pub. Date: Nov. 2, 1995

[30] Foreign Application Priority Data

Apr. 27, 1994 [GB] United Kingdom .................. 9408465

[51] Int. Cl.⁶ .................................................. C07H 21/04
[52] U.S. Cl. ............................ 435/6; 514/297; 536/24.31
[58] Field of Search ................................ 435/6; 424/468; 514/297; 536/24.31

[56] References Cited

U.S. PATENT DOCUMENTS

| | | |
|---|---|---|
| 5,508,167 | 4/1996 | Roses et al. . |
| 5,576,022 | 11/1996 | Yang et al. . |
| 5,643,960 | 7/1997 | Breitner et al. . |
| 5,698,224 | 12/1997 | Guittard et al. . |

FOREIGN PATENT DOCUMENTS

| | | |
|---|---|---|
| WO 94 09155 | 4/1994 | WIPO . |
| WO 95 29257 | 11/1995 | WIPO . |
| WO 96 02670 | 2/1996 | WIPO . |
| WO 96 03656 | 2/1996 | WIPO . |

OTHER PUBLICATIONS

Higgins, G.A. et al., *Pharmacology Biochemistry and Behavior*, 56(4):675–685, 1997.

Brion, J.P., *Acta Clinica Belgica*, 51(2): 80–90, 1996.

Farlow, M.R. et al., *Ann. N.Y. Acad. Sci.*, 802 : 101–110, 1996.

Sorbi et al., "ApoE as a diagnostic factor for post–traumatic coma," *Nature Medicine*, 1(9):852 (1995).

Corder et al., "Gene Dose of Apolipoprotein E Type 4 Allele and the Risk of Alzheimer's Disease in Late Onset Families", Science 261:921–923, 1993.

Knapp et al., "A 30–week Randomized Controlled Trial of High–dose Tacrine in Patients with Alzheimer's Disease", J. American Medical Assoc. 271:985–991, 1994.

Liddel et al., "Confirmation of Association Between the e4 allele of APO E and Alzheimer's Disease", J. Medical Genetics 31:197–200, 1994.

Mahley et al., Biochem. Biophys. Acta. 737:197–222, 1983.

Noguchi et al., "Apolipoprotein E Genotype and Alzheimer's Disease" Lancet (letter) 342:737, 1993.

Payami et al., "Apolipoprotein E and Alzheimer's Disease", Lancet (letter) 342:738, 1993.

Poirier et al., "In: Basic and Therapeutic Strategies in Alzheimer's and Parkinson's Diseases", Plenum Press 191–194, 1991.

Poirier et al., "Cholesterol Synthesis and Lipoprotein Reuptake During Synaptic Remodelling In Hippocampus in Adult Rats", Neuroscience 55:81–90, 1993.

Poirier et al., "Apolipoprotein E Polymorphism and Alzheimer's Disease", Lancet 342:697–699, 1993.

Poirier et al., "Astrocytic Apolipoprotein E mRNA and GFAP mRNA in Hippocampus After Entorhinal Cortex Lesioning", Mol. Brain Res. 11:97–106, 1991.

Poirier et al., "Cloning of Hippocampal poly(A) RNA Sequences that Increase After Emtorhinal Cortex Lesion in Adult Rat", Mol. Brain Res. 9:191–195, 1991.

Roheim et al., "Apolipoproteins in Human Cerebrospinal Fluid", Proc. Natl. Acad. Sci. 76:4646–4649, 1979.

*Primary Examiner*—Marianne P. Allen
*Attorney, Agent, or Firm*—Clark & Elbing LLP; Kristina Bieker-Brady

[57] ABSTRACT

The present invention relates to a method for the identification of human subjects to be responsive to cholinomimetic therapy comprising determining the absence of apolipoprotein E4 (apoE4) alleles in a biological sample of the patient where the absence of at least one apoE4 allele indicates a predisposition to respond to cholinomimetic therapy and methods of administering cholinomimetics to such identified subjects.

4 Claims, 12 Drawing Sheets

APOLIPOPROTEIN E POLYMORPHISM AND TREATMENT OF ALZHEIMER'S DISEASE

BACKGROUND OF THE INVENTION (a) Field of the Invention

The invention relates to a method for the treatment of Alzheimer's disease in a patient based on the cholinergic activity in the brain.

(b) Description of Prior Art

Apolipoprotein E (apo E) functions as a ligand in the process of receptor mediated internalization of lipid-rich lipoproteins, and it is probably also involved in reverse lipid transport (Mahley R. W. et al., 1983, *Biochem. Biophys. Acta.* 737:197–222). In the central nervous system (CNS), apoE plays a central role in the mobilization and redistribution of cholesterol and phospholipid during membrane remodeling associated with synaptic plasticity (Poirier J. et al., 1991, *Mol. Brain. Res.,* 9:191–195; Poirier J. et al., 1991, *Mol. Brain. Res.,* 11:97–106; Poirier J. et al., 1993, *Neuroscience,* 55:81–90). The importance of apoE in the brain is further underscored by the absence of other key plasma apolipoproteins such as apo A1 and apo B (Roheim P. S. et al., 1979, *Proc. Natl. Acad. Sci.,* 76:4646–4649) in this tissue. ApoE mRNA is found predominantly in astrocytes in the CNS.

The apoE gene on chromosome 19 has three common alleles (E2, E3, E4), which encode three major apoE isoforms. Recently, the frequency of the apoE4 allele was shown to be markedly increased in sporadic (Poirier J. et al., 1993, Apolipoprotein E phenotype and Alzheimer's Disease, *Lancet,* 342:697–699; Noguchi S. et al., 1993, *Lancet* (letter), 342:737) and late onset familial Alzheimer's disease (AD) (Corder E. H. et al., 1993, *Science,* 261:921–923; Payami H. et al., 1993, *Lancet* (letter), 342:738). A gene dosage effect was observed in both sporadic and familial cases (i.e. as age of onset increases, E4 allele copy number decreases). Women, who are generally at a greater risk of developing Alzheimer's disease, show increased E4 allele frequency when compared to age matched men.

Preliminary studies have shown that apoE mRNA levels are relatively unchanged (Poirier J. et al., 1991, In: *Basic and therapeutic strategies in Alzheimer's and Parkinsons's diseases,* T. Nagatsu, F. Abraham. eds., New York, Plenum Press, 191–194) in post-mortem brains of AD patients. These results were obtained from patients whose genotypes were undetermined.

It would be highly desirable to be provided with means to determine the cholinergic activity in the brain of Alzheimer's disease patients to determine if cholinomimetics-based therapies should be carried out.

SUMMARY OF THE INVENTION

One aim of the present invention is to provide with means to assess the cholinergic activity in the brain of Alzheimer's disease patients to determine if cholinomimetics-based therapies should be carried out.

In accordance with the present invention there is provided a method for the treatment of Alzheimer's disease in a genetically characterized Alzheimer's patient for its pre-disposition to respond to cholinomimetic therapies, which comprises:

a) determining the presence of apolipoproteins E2 and E3 allele or the absence of apolipoprotein E4 allele from peripheral tissues of the patient which is indicative of the degree of impairment in brain acetylcholine synthesis and nicotinic receptor activity; and b) administering to the patient a suitable therapeutic agent relative to the degree of impairment of step a).

Therapeutic agents to be used in accordance with the present invention may be selected from the group consisting of inhibitors of acetylcholine degradation, inducers of acetylcholine synthesis, acetylcholine agonists or mimics, and muscarinic M2-receptor antagonists.

In accordance with the present invention there is also provided a method for the identification of human subjects with cognitive impairments due to age, Alzheimer's disease or other neurodegenerative diseases, to be responsive to cholinomimetic therapies, which comprises determining the number of copies of the apoE2 and apoE3 gene alleles or the absence of apoE4 gene allele in a biological sample of the patient directly by using appropriate apoE2 and apoE3 probes or indirectly by phenotyping, and wherein the presence of apoE2 and/or apoE3 gene alleles and the absence of apoE4 indicate a pre-disposition to respond to cholinomimetics-based therapies.

In accordance with the present invention there is provided a method for the identification of Alzheimer's patient to be responsive to cognitive enhancers and cholinomimetic therapies, which comprises determining the number of copies of the apoE2 and apoE3 gene alleles in a biological sample of the patient directly by using appropriate apoE2 and apoE3 probes or indirectly by phenotyping, and wherein the presence of apoE2 and/or apoE3 gene alleles and the absence of apoE4 indicate a pre-disposition to respond to cholinomimetics-based therapies indicates a predisposition to respond to cholinomimetics-based therapies.

For the purpose of the present invention the following terms are defined below.

The term "cognitive enhancers" is intended to mean that these drugs enhance a) memory performance, whether it is verbal memory, spatial memory or factual memory and b) learning capacity.

The term "cholinomimetic therapies" is intended to mean drugs that mimic the function of acetylcholine or enhance the activity of remaining acetylcholine synthesizing cells. These drugs include, but are not limited to, inhibitors of acetylcholine degradation (acetylcholine esterase inhibitors like tacrine), drugs that mimic acetylcholine structure and function (agonist: muscarinic M1-receptor agonist is a typical example), drugs that block acetylcholine uptake by neurons and drugs that interact pre-synaptic receptors to induce acetylcholine release from cholinergic neurons.

The term "appropriate apoE2 and apoE3 probes" refers to nucleic acid primer sequences that selectively recognize the apoE3 or apoE2 allele on chromosome 19 and that can be used to selectively amplify (by PCR) these different mutations of the apoE gene.

DETAILED DESCRIPTION OF THE INVENTION

Apolipoprotein E (apoE) is important in modulating cholesterol and phospholipid transport from one cell to another. ApoE binds with great affinity to the apoE/apoB LDL receptor to mediate the internalization and catabolism of cholesterol- and phospholipid-containing lipoproteins. It is a polymorphic protein with three common alleles coding from apoE2, apoE3 and apoE4. Recently, the apoE4 allele was shown to be associated with sporadic and late-onset familial Alzheimer's disease (AD). The present study demonstrates that the apoE4 allele has little or no effect on apoE mRNA levels and protein content in the hippocampus of AD. However, we show a strong and significant correlation between the apoE4 allele copy number and the amyloid plaque counts in the CA1, subiculum and parasubiculum areas. More importantly, we found that the presence of the apoE4 allele has a dramatic impact on the residual activity of choline acetyltransferase (ChAT), the enzyme involved in the synthesis of acetylcholine. A marked reduction in ChAT activity was found in both the hippocampus and the temporal cortex of humans with the apoE genotype 4/3 when compared to those with the genotype 3/3. All apoE4/3 individuals (except one) suffered from AD. Interestingly, most AD cases with apoE genotype 3/3 show ChAT activities near normal values. The reduction in ChAT activity is apparently caused by a selective loss of neurons synthesizing acetylcholine in the nucleus basalis of Maynert and in the diagonal band of Broca. These results support the involvement of apoE4 in the pathogenesis of AD and provide for the first time a possible explanation for the heterogeneity of cholinergic dysfunctions reported in sporadic AD.

Because apoE expression (mRNA and protein levels) is markedly increased in the hippocampus of entorhinal cortex lesioned rats (Poirier J. et al., 1991, *Mol. Brain. Res.*, 9:191–195; Poirier J. et al., 1991, *Mol. Brain. Res.*, 11:97–106; Poirier J. et al., 1993, *Neuroscience*, 55:81–90) and in humans with multiple sclerosis, we examined apoE mRNA and protein levels in the hippocampus of AD patients whose genotypes has previously been established.

Figure 1:
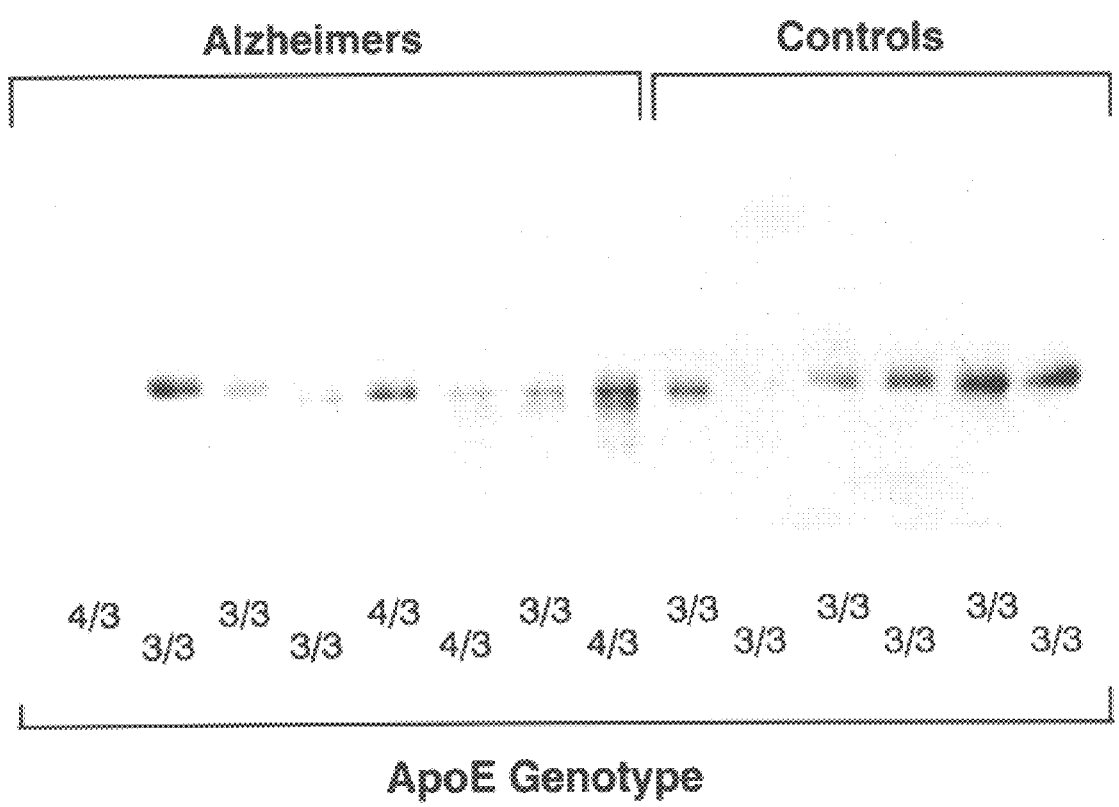
FIG. 1 is a Western blot analysis of apoE protein levels in the hippocampus of Alzheimer's and control individuals.
Figure 2:
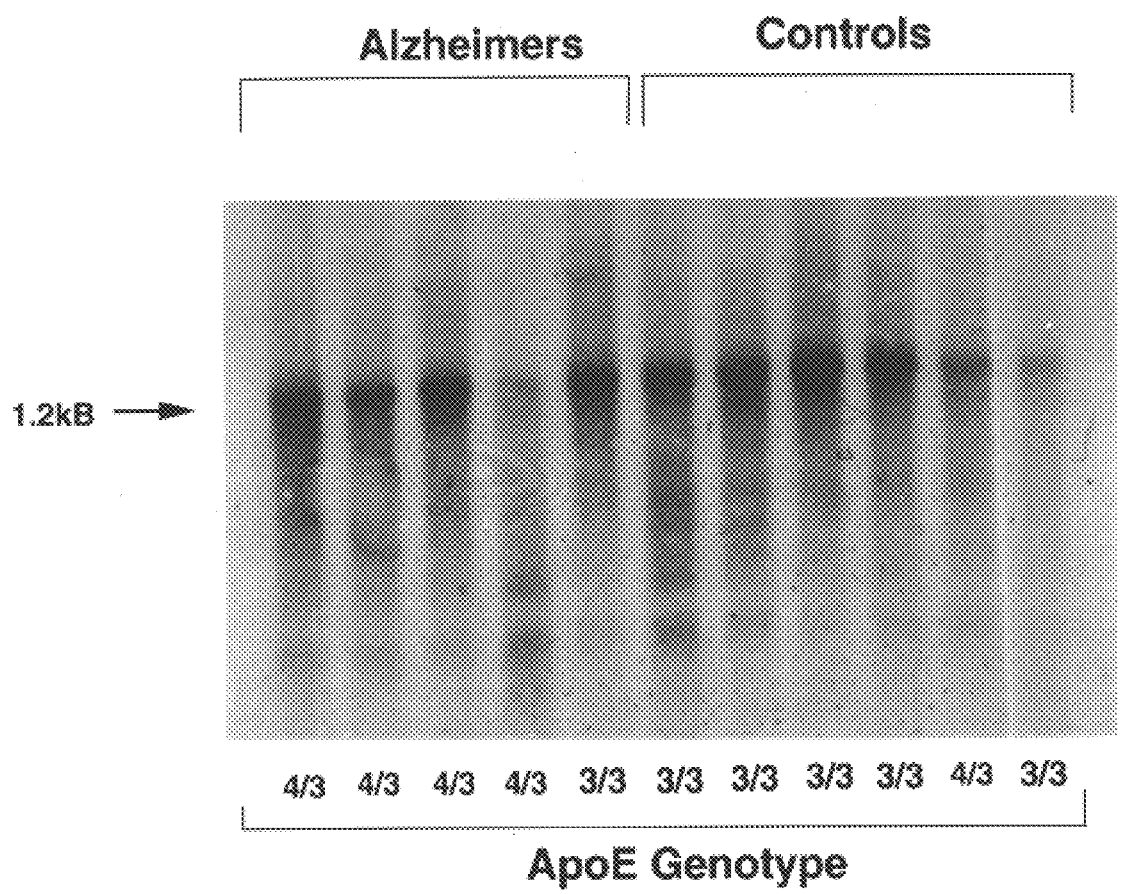
FIG. 2 is a Northern blot analysis of the apoE mRNA expression in the hippocampus of AD and control individuals.
Figure 3A:
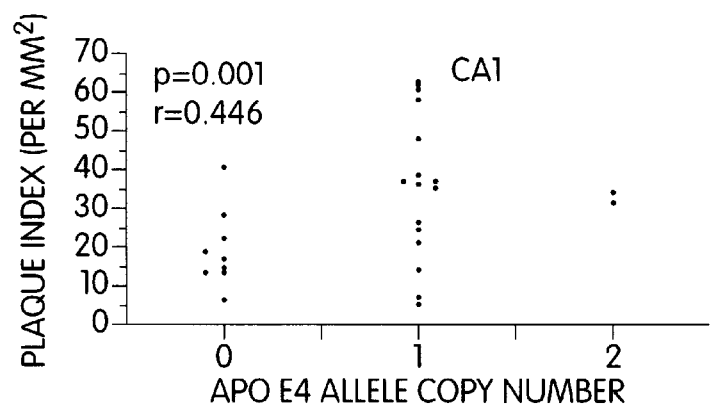
FIG. 3A–F illustrates Apolipoprotein E4 allele copy number, tangles and senile plaque densities in the hippocampus in Alzheimer's disease.
Figure 3B:
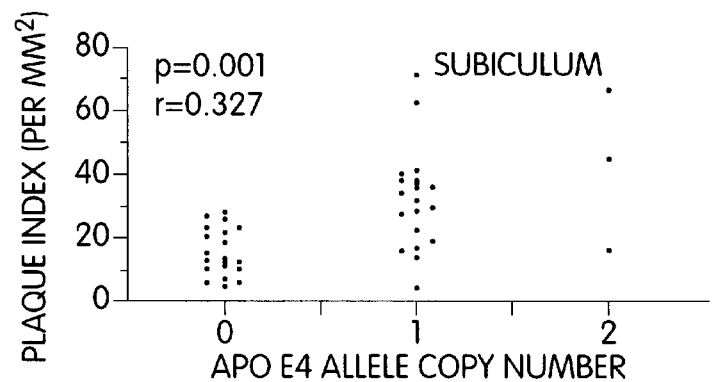
Figure 3C:
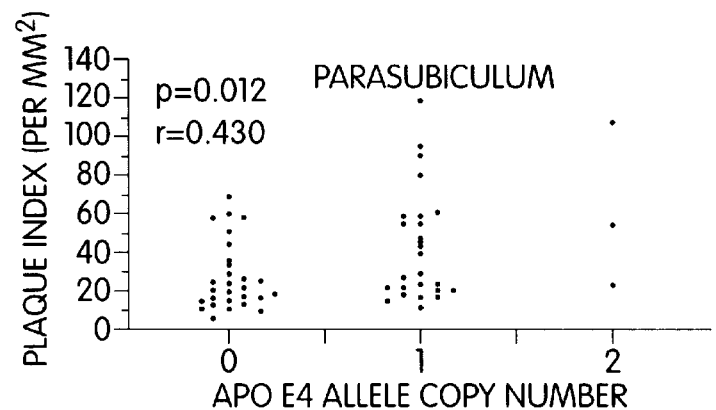
Figure 3D:
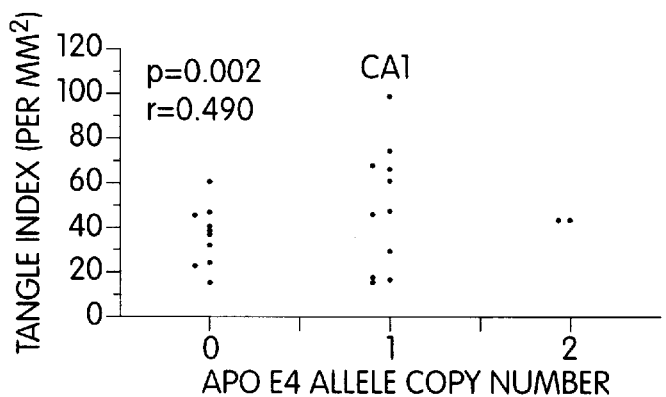
Figure 3E:
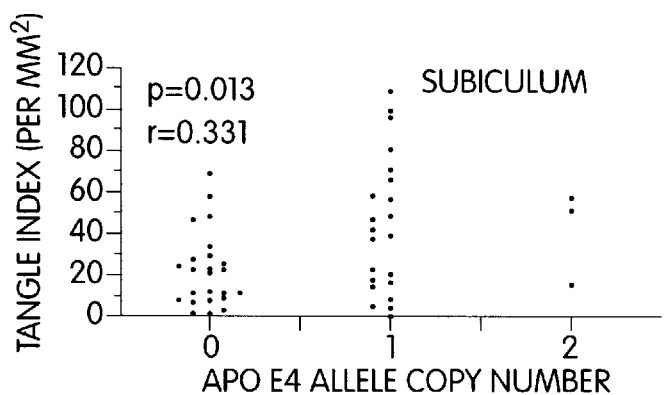
Figure 3F:
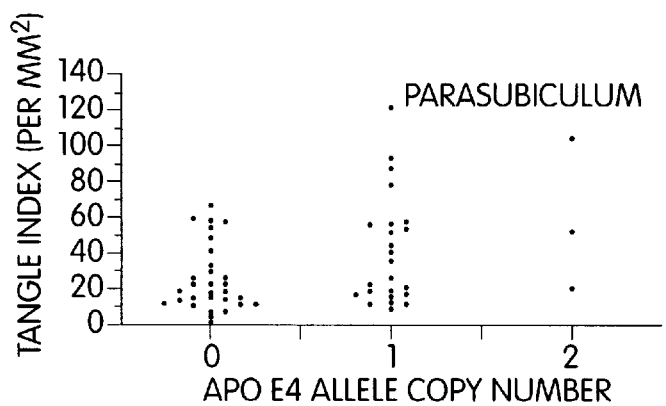

FIGS. 1 and 2 illustrate Western and Northern blot analyses of apoE levels in the hippocampus of control and AD patients as a function of their respective genotype.

Frozen hippocampi from post-mortem control and AD patients were obtained from the Douglas Hospital Brain Bank in Montréal. Age and sex were matched and post-mortem delays were similar from the two groups (~14 hrs). Post-mortem delays up until 24 hours have little impact on apoE stability (Lehtimaki T., 1991, *Clin. Chim. Acta*, 203:177–182) and it can be stored at −80° C. for several months without noticeable trace of degradation. Hippocampal total RNA was extracted and quantified by oligo(dT) hybridization as described previously (Poirier J. et al., 1991, *Mol. Brain. Res.*, 11:97–106). Hybridization protocol of the full length apoE cRNA probe used in these experiment was described before (Poirier J. et al., 1991, *Mol. Brain. Res.*, 9:191–195). High molecular weight DNA was isolated from frozen cerebellum or temporal cortex as adapted from Goelz et al. (Goelz S. E. et al., 1986, *Biochem. Biophys. Res. Comm.*, 130:118–126).

ApoE genotype was determined by allele-specific extension of purified brain DNA using a modification of the method of Main et al. (Main R. F. et al., 1991, *J. Lipid. Res.*, 32:183–187). The primers labeled D, E, F, G, and H were synthesized for us by Genosys Biotech (The Woodland, TX); the primer sequences are given in Main et al. (Main R. F. et al., 1991, *J. Lipid. Res.*, 32:183–187). Reactions were carried out in a volume of 50 uL containing 1 ug of DNA; deoxyadenosine triphosphate, deoxycytidine triphosphate, deoxythymidine triphosphate and deoxyguanosine triphosphate, each 0.2 mmol/L; 10% dimethyl sulfoxide; 12.5 pmol of either primer D, E, F, G,; 25 pmol of primer H; and 10 uL of 10 PCR reaction buffer (Vector Biosystem, Toronto, ONT.). The DNA in the reaction mixture was first denatured for 10 min. at 96° C. and then cooled to 4° C. One unit of Taq polymerase (Vector Biosystem, Toronto, ONT.) was then added to each sample. Each sample was reheated for 2 min. at 96° C. and subjected to 30 cycles in a thermal cycler with each cycle consisting of a 10 sec denaturation at 96° C., 30 sec annealing at 58° C. and 1 min. extension at 65° C. The reaction products were visualized by electrophoresis of 10 uL of the reaction mixture in a 1% agarose gel containing TPE buffer (0.08 mol/L Tris-phosphate, 0.002 mol/L EDTA) and ethidium bromide (0.15 ug/mL) for 1 hr at 67 v. The gel were then photographed and the banding profile was compared to known standards.

Briefly, 50 ug of hippocampal homogenate, pretreated with 1 u of neuraminidase, were loaded on a 25 cm long SDS polyacrylamide gel (10%) and run for 3 hours at room temperature. Proteins were transferred on nitrocellulose filter in the BIORAD™ Transblot cell and detection of the apoE band was done with a polyclonal antibody raised against human apoE (International Immunology Corp., CA, Dil. 1:2000). Adsorption of the antibody with purified apoE completely blocked the detection of the human apoE band at MW 34–36 kDa. Molecular weight markers (Rainbow markers, Amersham) were run in adjacent wells while visualization of the bands was done with a chemiluminescence detection kit (Amersham, Cat. No. RPN 2100). Quantification of the autoradiographic signals was done on the MCID image analysis system (Ste-Catherine, Ontario) equipped with the 1D-gel analysis software.

Autoradiographic analyses of the band corresponding to apoE revealed no differences between control and AD hippocampal tissues, whether the apoE4 allele is present or not. These results are in agreement with a previous report (Poirier J. et al., 1991, In: *Basic and therapeutic strategies in Alzheimer's and Parkinsons's diseases*, T. Nagatsu, F. Abraham. eds., New York, Plenum Press, 191–194) which showed that despite astrocytic hyperreactivity and increases in astrocytic glial fibrillary acidic protein mRNA levels in the hippocampus of AD, apoE gene expression remained unchanged in the hippocampus. The increased expression of GFAP is often used as marker of ongoing differentiation and/or neurodegeneration (Poirier J. et al., 1991, *Mol. Brain. Res.*, 9:191–195). Thus, these results suggest that despite marked deafferentation and cell loss in the hippocampus of AD (Hyman BT et al., 1984, *Science,* 225, 1168–1170), apoE gene expression remains unaltered. Moreover, the presence of a single copy of the E4 allele in the brain appears to have little or no effect on the steady state levels of apoE in AD.

The in vivo metabolism of apoE4 in the circulation has been shown to be kinetically different from apoE3 in humans (Gregg R. E. et al., 1986, *J. Clin. Invest.,* 87:815–821). The E4 allele is associated with abnormally high levels of circulating lipoproteins, increased plasma and LDL cholesterol amounts, altered lipoprotein distribution, decreased plasma apoE in patients homozygote for E4, and rapid catabolism of apoE4 compared to apoE3 (Gregg R. E. et al., 1986, *J. Clin. Invest.,* 87:815–821). This may suggest that apoE4 is metabolically different from apoE3 and could thus explain disturbances in lipid homeostasis reported in the AD brain. For example, phosphatidylcholine (PC), phosphatidylethanolamine (PE) and cholesterol levels are all significantly reduced in AD brains (Pettegrew J. W., 1989, *Ann. NY Acad. Sci.,* 568:5–28). Moreover, the levels of phosphatidylcholine, phosphatidyl ethanolamine and cholesterol have been inversely correlated with the number of senile plaques between cortical layer II and IV (Pettegrew J. W., 1989, *Ann. NY Acad. Sci.,* 568:5–28). Accordingly, we examined the effect of apoE4 allele copy number on the incidence of senile plaques and neurofibrillary tangles in the hippocampus of 59 AD patients.

FIG. 3 illustrates the correlations between apoE4 allele copy number and senile plaques and neurofibrillary tangles in three different areas of the hippocampus, namely the CA 1 sub-field, subiculum and the parasubiculum in individuals with different apoE4 allele copy number.

Genotype was determined as described for FIG. 1. Senile plaque and tangle density measures were performed as described before (Aubert I. et al., 1992, *J. Neurochem.,* 58:529–541). Paraffin embedded hippocampal tissue from 59 autopsied AD patients was obtained from the Douglas Hospital Brain Bank and stained with hematoxylin and eosin, modified Bielchowsky, and alkaline Congo red. Quantitative morphometric evaluations of neurofibrillary tangles and senile plaques were done as follows. A micrometric scale was used for calibration. Readings were done with a 10 X objective for plaques and 25X objective for tangles. Diffuse plaques were excluded from these measurements. Screening of alkaline Congo™ red stains under polarized light was used to control the reliability of tangle staining and, to a lesser extent, of senile plaque's affinity for the modified Bielchowsky preparation. Idiopathic Parkinson's disease (IPD) was diagnosed according to the presence of significant loss of pigmented neurons, Lewy bodies in residual neurons, clusters of macrophages, and gliosis in the pars compacta of the substantia nigra. These usually correlated with pre-mortem classical features of IPD, such as resting tremor, rigidity, and akinesia. Statistical analysis was performed using the Multivariate General Linear™ Models as part, of the Systat Statistical Software™ package.

The correlation between apoE4 allele copy number and the density of senile plaque is very strong in all three hippocampal regions. The correlation between apoE4 allele copy number and the neurofibrillary tangles index was also significant for the CA1 and the subiculum areas. These results support the concept that apoE4 plays a role in the pathophysiology of AD.

Brain phospholipids such as PC and PE which have been shown to play an important role in the availability of choline, the rate-limiting precursor of acetylcholine (Ach). Brain levels of choline are decreased by 40–50% in AD frontal and parietal cortex (Nitch RM et al., 1992, *Proc. Natl. Acad. Sci.,* 89:1671–1675). Similarly, cholesterol is apparently required for the proper function of some cholinergic receptor sub-types (Jones O. T. & McNamee M. G., 1988, *Biochemistry,* 27:2364–2374). On the basis of possible interrelationships between apoE4, senile plaque and neurofibrillary tangle counts and Ach, we evaluated the next possible association between the presence of apoE4 and cholinergic dysfunction, a classical hallmark of AD (Bowen DM et al., 1981, *N. Engl. J. Med.,* 305:1016; Whitehouse PJ et al., 1982, *Science,* 215:1237). We focused our attention on the determination of ChAT activity, the key enzyme involved in the synthesis of Ach, in post-mortem hippocampus and temporal cortex of individuals suffering from AD and in control subjects.

Figure 4A:
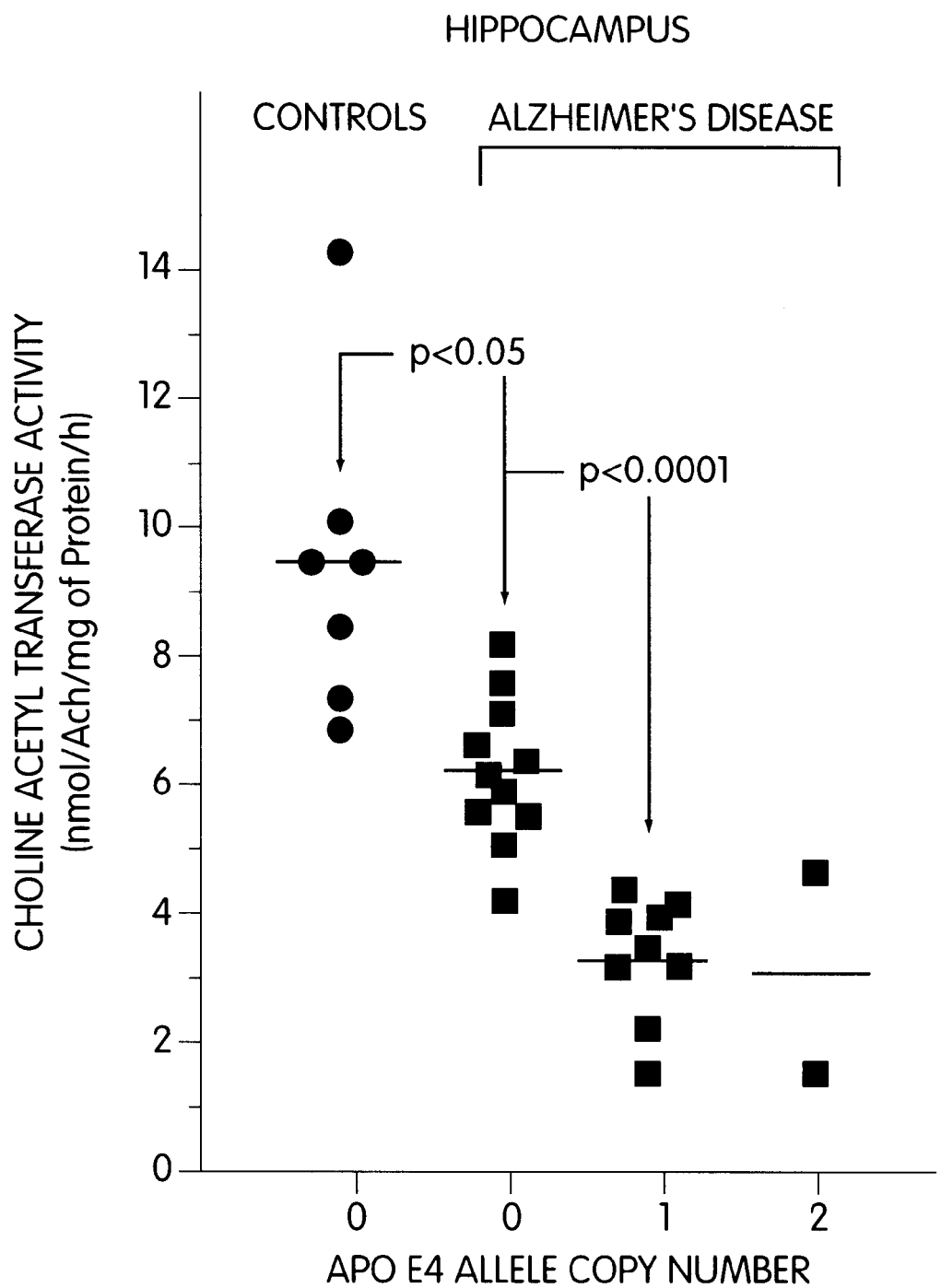
FIG. 4A–B illustrates Apolipoprotein E4 allele copy number and choline acetyltransferase activity in Alzheimer's disease.
Figure 4B:
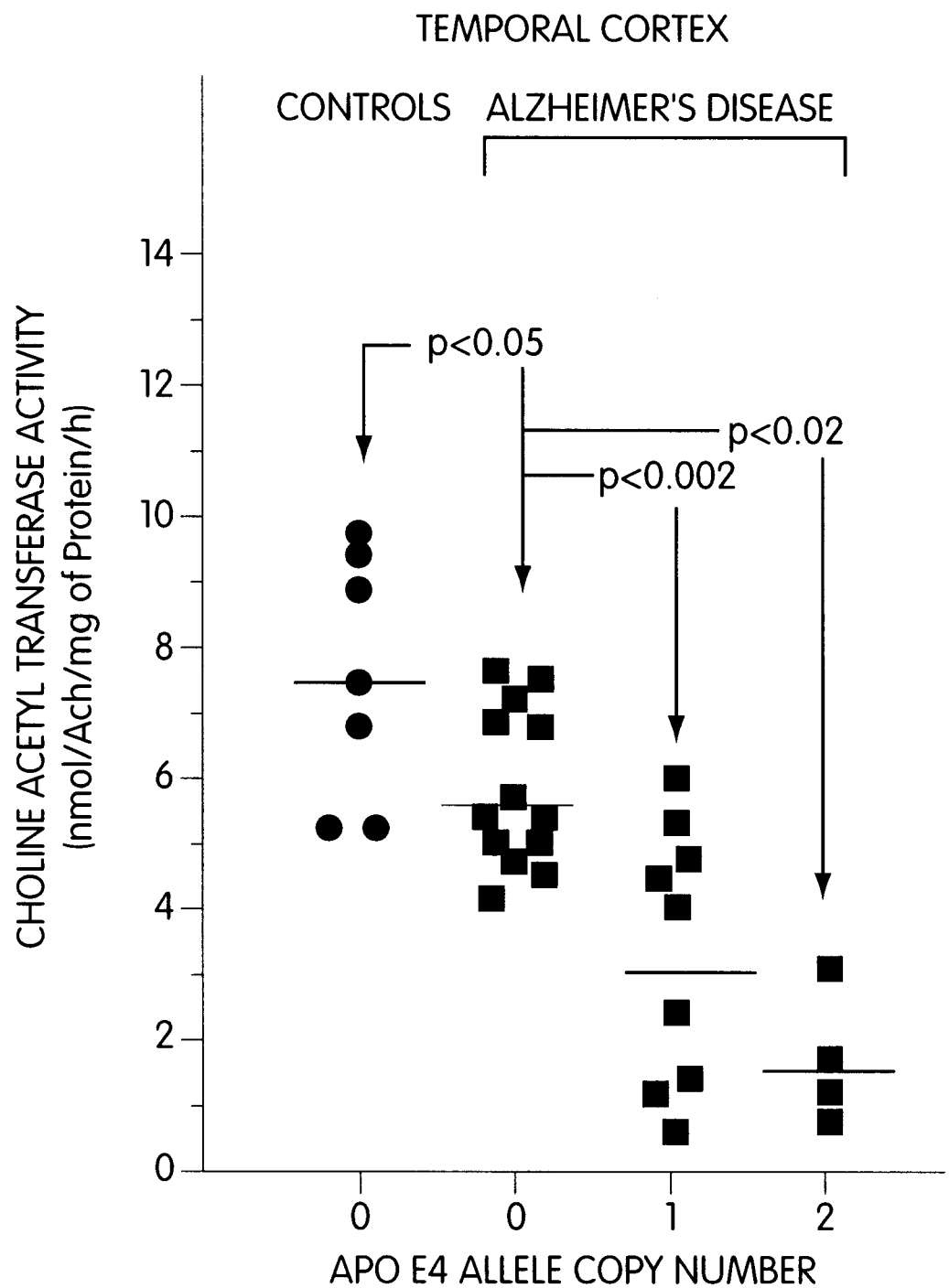

FIGS. 4 and 6 illustrate the effect of the presence of apoE4 isoform on hippocampal and temporal cortex ChAT activity.

Left hemisphere to be used for biochemical assays were sectioned in to thick (10 mm) coronal slices quickly and deeply frozen in 2-methylbutane at $-40°$ C. before storage at $-80°$ C. Tissues from hippocampal and temporal cortical areas were homogenized and incubated for 15 min. in buffer containing [$^{14}$C] acetyl-CoA as previously described in detail elsewhere (Aubert I. et al., 1992, *J. Neurochem.,* 58:529–541). The post-mortem diagnostic was performed as described for FIG. 3. Apolipoprotein E genotype was determined as described for FIG. 1.

Highly significant reductions in ChAT activity were seen in apoE4 carriers. In the hippocampus (22 ADs and 7 controls), ChaT activity values are 9.44±0.93 (control apo E3/3, no apoE4 allele), 6.09±0.36 (AD apoE3/3, no apoE4 allele), 3.21±0.31 (AD apoE4/3) and 2.94±1.52 (AD apoE4/4) nmol ACh/mg protein/hr, respectively. Statistical analyses indicate that control apoE3/3 ChAT values are significantly different from the AD apoE3/3 group ($p<0.05$) and the apoE4/3 group ($p<0.0001$) whereas, AD apoE3/3 ChAT levels are significantly different from the AD apoE4/3 group ($p<0.0001$) and likely the apoE4/4 group, although statistical evaluation could not be performed because of the limited number of apoE4 homozygotes available. Similar results were obtained in the temporal cortex (26 ADs and 7 controls) with ChAT activity values of 7.48±0.74 (control apoE3/3), 5.65±0.33 (AD apoE3/3), 2.91±0.66 (AD apoE4/3) and 1.56±0.47 (AD apoE4/4) nmol ACh/mg protein/hr, respectively. Statistical analyses indicate that control apoE3/3 ChAT values are significantly different from all AD groups ($p<0.05$ for apoE3/3 and $p<0.001$ apoE4/3) whereas AD apoE3/3 ChAT levels are significantly different from the AD apoE4/3 group ($p<0.002$) and the apoE4/4 group ($p<0.02$).

Figure 5A:
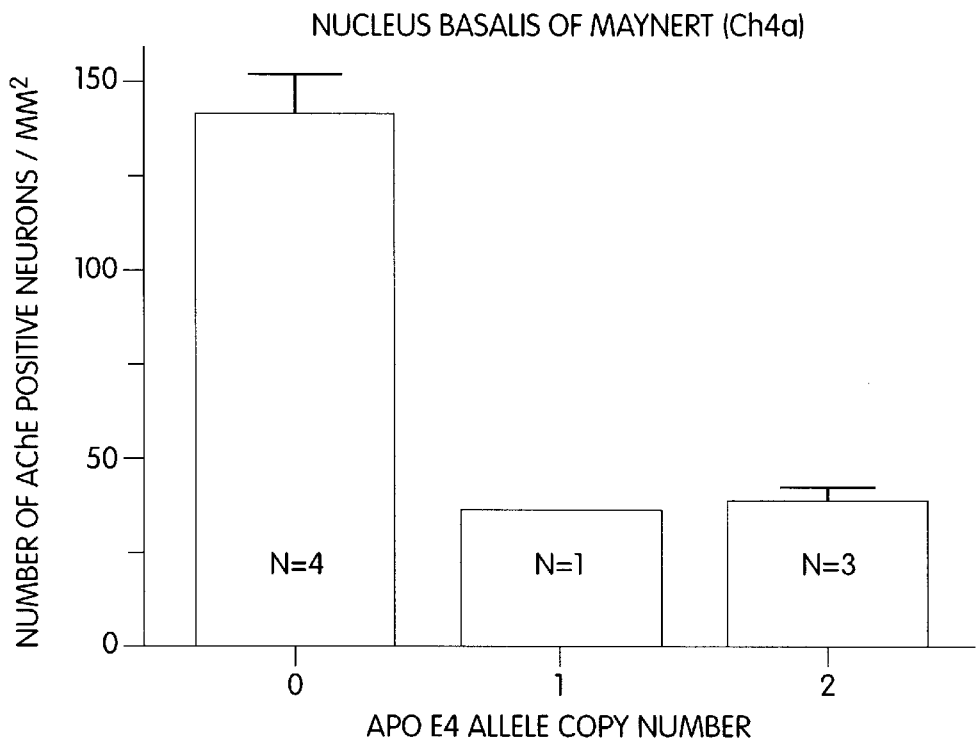
FIG. 5A–B illustrates the loss of neurons which synthesize acetylcholine in the nucleus basalis of Maynert and in the diagonal band of Broca.
Figure 5B:
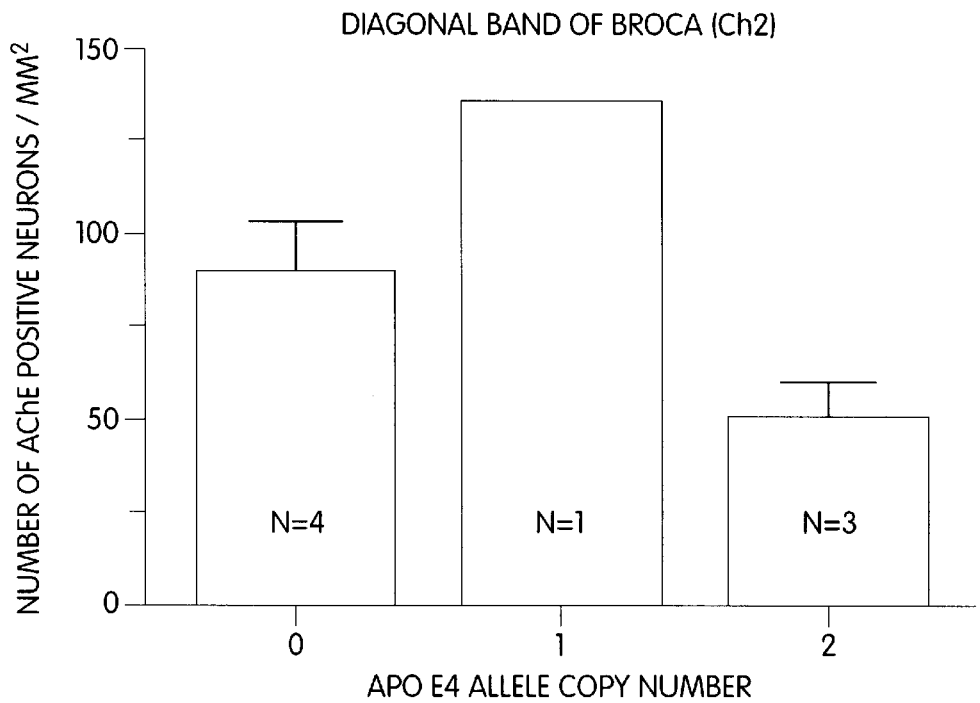
Figure 6A:
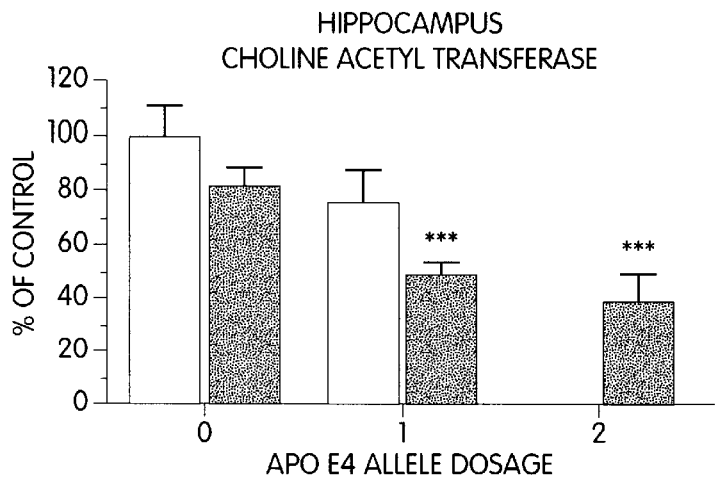
FIG. 6A–J illustrates the effect of apolipoprotein E4 (apo E4) allele copy number on a) choline acetyltransferase activity, b) nicotinic receptor density, c) total muscarinic receptor density, d) muscarinic M1 (post-synaptic) and e) muscarinic M2 receptor density in post-mortem control and Alzheimer's disease brains in the hippocampal formation and temporal cortex.
Figure 6B:
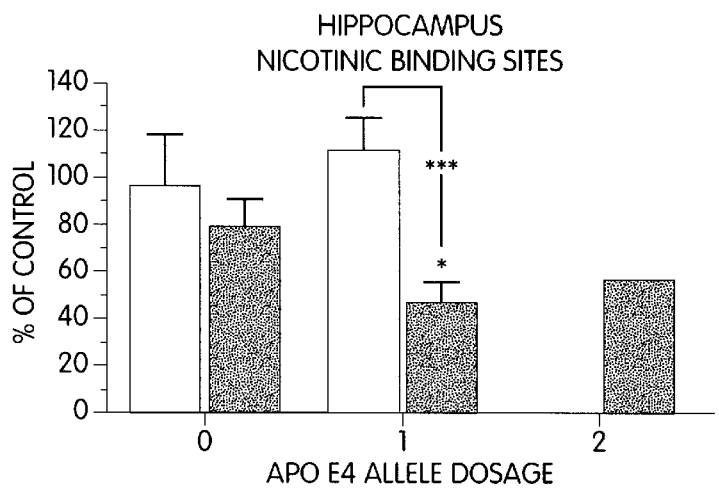
Figure 6C:
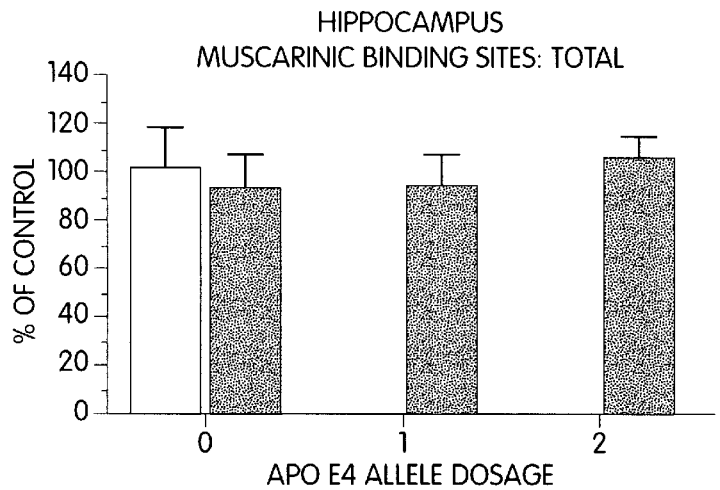
Figure 6D:
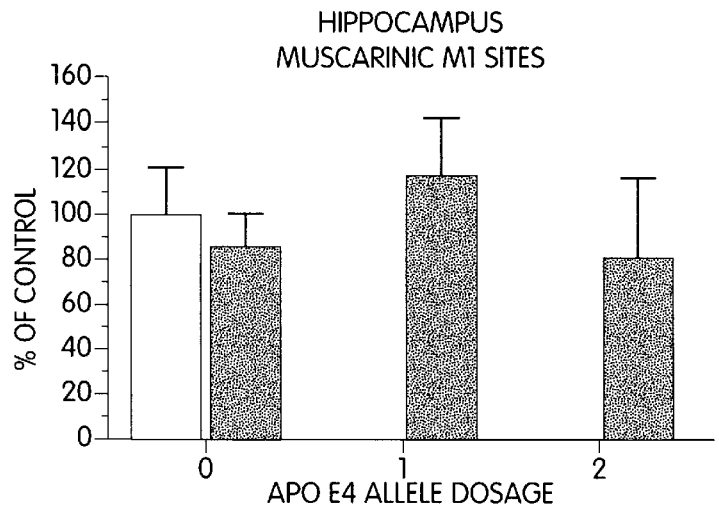
Figure 6E:
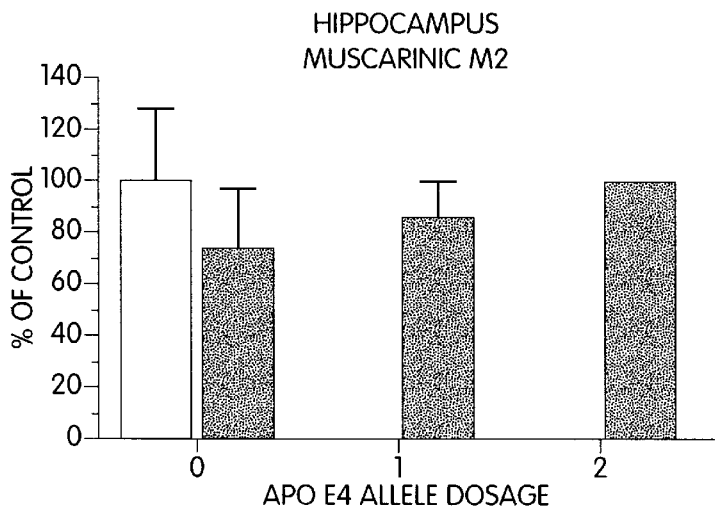
Figure 6F:
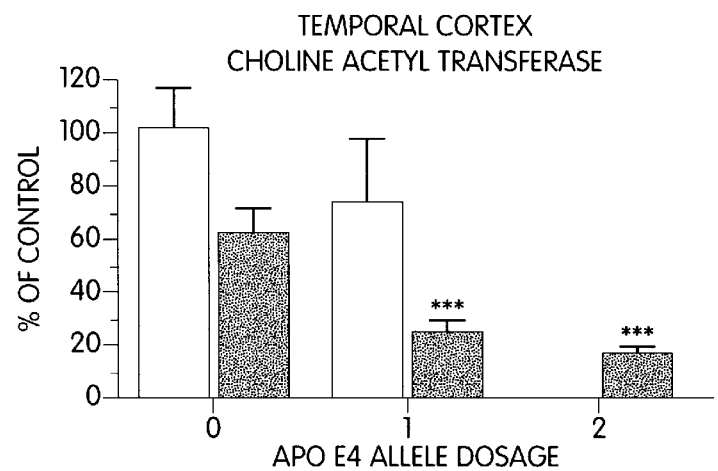
Figure 6G:
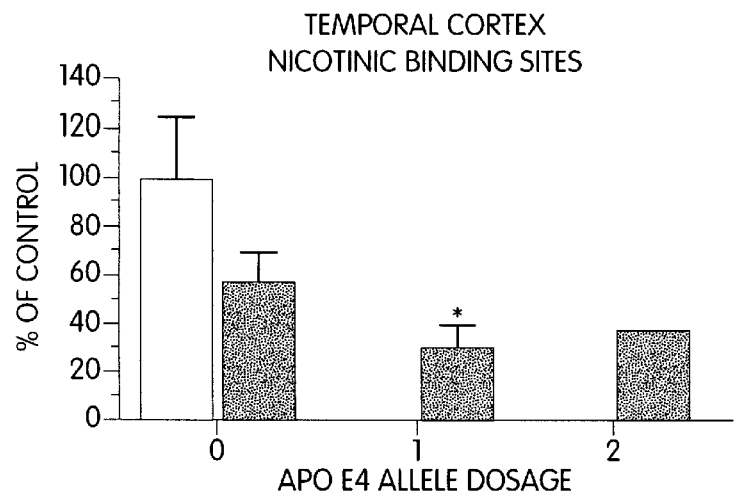
Figure 6H:
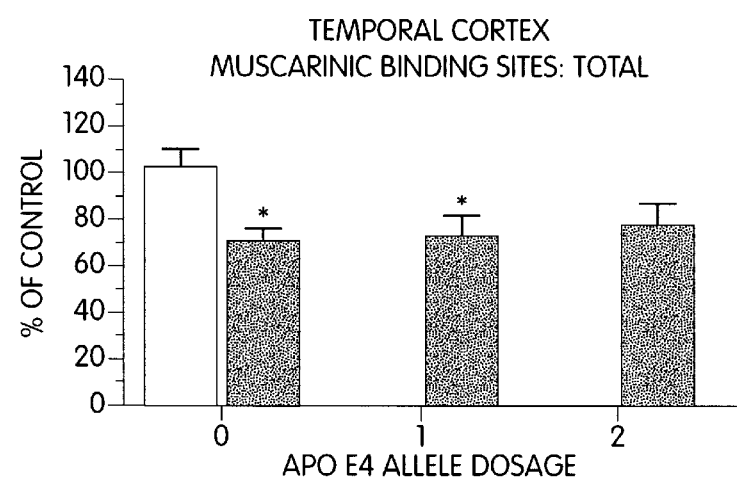
Figure 6I:
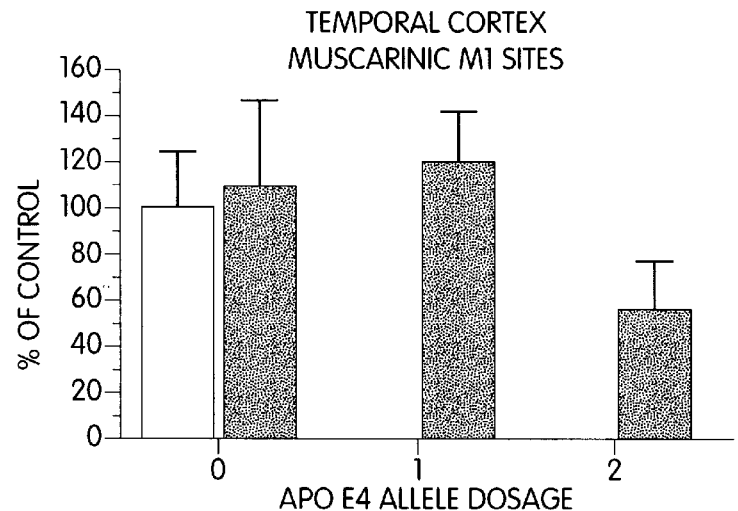
Figure 6J:
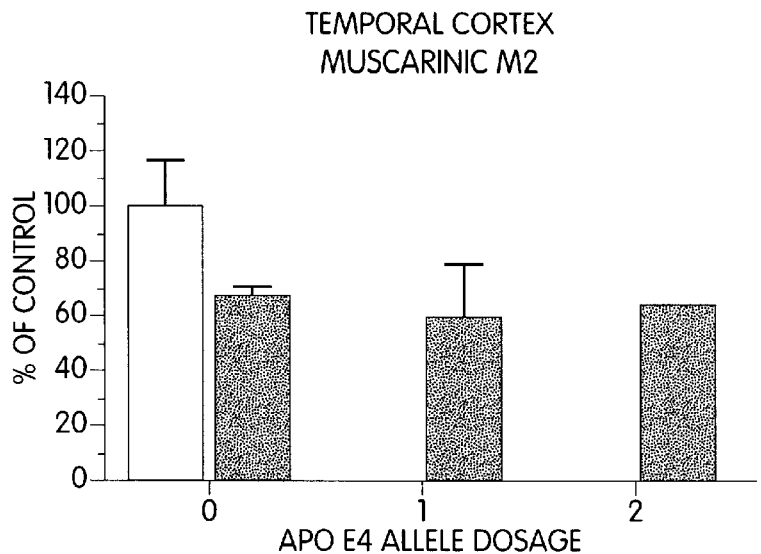

The apoE4 allele copy number-related reduction in ChAT activity could be caused by at least two distinct phenomena. First, phospholipids such as PC and PE which can serve as precursors to choline in the synthesis of Ach could be transported into neurons via the classical apoE-LDL receptor pathway. An isoform-dependent impaired regulation of the transport of phospholipids in the brain of apoE4 carriers could explain the reduced levels of PC, PE and choline reported in AD; this then leading to decreased Ach synthetic capacities. Alternatively, the reduction in neuronal ChAT activities and choline levels could be secondary to losses of cholinergic neurons in the basal forebrain, including the nucleus basalis of Meynert (NBM), diagonal band of Broca (DBB) and the septal area. Analysis of the number of acetyl-cholinesterase-positive neurons in the NBM and DBB of a small number of AD patients (n=7) revealed marked losses of cholinergic neurons in apoE4 versus apoE3 homozygous AD cases (↓70% in NBM and ↓45% in DBB, FIG. 5).

These results clearly indicate that there are distinct genetic entities in sporadic AD which show differential degrees of alterations of cholinergic activity, at least as revealed by ChAT activity. Our data also suggest that cholinergic function in AD-E3/3 bearers may be spared and that these patients could be better responders to a cholinomimetic-based therapy; which hypothesis will be discussed in detail below. The cholinergic hypothesis of geriatric memory dysfunction as reviewed by Bartus and colleagues more than a decade ago (Bartus R. T. et al., 1982, Science, 217:408–417) raised some fundamental questions regarding the heterogeneity of responses toward different cholinomimetics in AD. The absence of clear beneficial effects of choline and lecithin on geriatric patients with and without AD is still perplexing. Furthermore, multiple clinical studies using esterases inhibitors such as physostigmine and tacrine have shown that contrary to young subjects, the optimal acute dose necessary to facilitate performance on memory tasks varied considerably among individual aged subjects (Bartus R. T. et al., 1982, Science, 217:408–417). In Example II below, the effect of apoE genotype on drug efficacy will be examined.

Thus, it appears that the presence of the apoE4 allele appears to be one of the key factors responsible for individual variations occurring in brain cholinergic systems and individual responses to cholinergic agents should be monitored in patients whose genotype has been determined. This issue will certainly have significant impact on the design of future clinical trials in AD. Prospective-retrospective analyses of AD patients which are either good or poor responders to cholinomimetics is discussed in Example II.

In conclusion, the presence of apoE4 was shown to be closely associated with three hallmarks of the pathophysiology of AD, namely senile plaques, tangles and ChAT activity. The relationships between apoE and these three established markers of AD pathology is highly dependent upon the number of copies of the E4 allele. These results could as well explained previous observations indicating that the apoE4 allele copy numbers is correlated to the age of onset in familial (Corder E. H. et al., 1993, Science, 261:921–923) and sporadic AD (Poirier J. et al., 1993, Apolipoprotein E phenotype and Alzheimer's Disease, Lancet, 342:697–699).

Finally, since the presence of apoE4 appears to have a direct impact on cholinergic activity in the brain, it is proposed that clinical trials involving cholinomimetics-based therapies should take into consideration the fact that genetically distinct entities exist in sporadic Alzheimer's disease and that they could explain the presence of either good and poor responders.

Furthermore, since cholinomimetic drugs may be used to enhance cognitive performances in non-Alzheimer's disease subjects (young and old), the results of the present invention indicate that cognitive performances could be restored, even enhanced by the administration of cholinomimetics such as acetyl-choline agonists (M1-agonist: xanomeline from Eli Lilly), M2receptors-antagonist (BIBN-99 from Boehringer Ingeilheim), inhibitors of acetylcholine degradation such as tacrine (Parke-Davis) or E-2020 (Pfizer) in subjects carrying apoE2 or apoE3 but not apoE4.

The present invention will be more readily understood by referring to the following examples which are given to illustrate the invention rather than to limit its scope.

EXAMPLE I

Additional Neurochemical Alterations and Therapeutic Response in Subjects Treated with Cholinominetics I. Post-Mortem Study of Cholineraic Marker Case Selection and apoE genotyping:

Frozen tissues from 84 autopsy confirmed cases of sporadic AD (35 females, 77.3±8.7 years: 49 males, 76.1±9.5 years) and from 14 control individuals (8 females, 71.6±3.6 years; 6 males, 66.4±3.1 years) were obtained from the Douglas Hospital Brain Bank in Montréal, Canada. The average post-mortem delay was 17.2±1.3 and 20.0±4.6 hours for AD and control subjects, respectively. It should be noted that the availability of apoE4/4 homozygous subjects is very limited, probably due to the fact that apoE4/4 homozygote individuals represent less than 1% of the entire population.

High molecular weight DNA for genotype analysis was isolated from frozen cerebellum or temporal cortex as adapted from (Nalbantoglu J. et al., 1994, Predictive value of apolipoprotein E4 mutation in Alzheimer's Disease, Ann. Neurol. 36:889–895). ApoE genotype was determined by allele-specific extension of purified brain DNA using (Nalbantoglu J. et al., 1994, Predictive value of apolipoprotein E4 mutation in Alzheimer's Disease, Ann. Neurol. 36:889–895). The primers labeled D, E, F, G, and H were synthesized for us by Genosys Biotech (The Woodland, TX); primer sequences are given in Main et al. (Main R. F. et al., 1991, J. Lipid. Res., 32:183–187). Reactions were carried out in a volume of 50 uL containing 1 ug of DNA; deoxyadenosine triphosphate, deoxycytidine triphosphate, deoxythymidine triphosphate and deoxyguanosine triphosphate (Pharmacia, Montreal, CANADA.), each 0.2 mmol/L; 10% dimethyl sulfoxide; 12.5 pmol of either primer D, E, F, G,; 25 pmol of primer H; and 10 uL of 10 PCR reaction buffer (Vector Biosystem, Toronto, CANADA). The DNA in the reaction mixture was first denatured for 10 min. at 96° C. and then cooled to 4° C. One unit of Taq polymerase (Vector Biosystem, Toronto, CANADA) was then added to each tube. Each sample was then reheated for 2 min. at 96° C. and subjected to 30 cycles in a thermal cycler with each cycle consisting of a 10 sec denaturation at 96° C., 30 sec annealing at 58° C. and 1 min. extension at 65° C. The reaction products were visualized by electrophoresis of 10 uL of the reaction mixture in a 1% agarose gel containing TPE buffer (0.08 mol/L Tris-phosphate, 0.002 mol/L EDTA, Sigma, St-Louis, USA) and ethidium bromide (0.15 ug/mL) for 1 hr at 67 v. The gels were then photographed and the banding profile was compared to known standards.

Neuropathological Analyses:

Neurofibrillary tangle and senile plaque indices were determined as described in detail elsewhere (Aubert I. et al., 1992, J. Neurochem., 58:529–541; Etienne P. et al, 1986, Neuroscience, 19:1279–1291). Fifteen micron paraffin embedded hippocampal sections were stained with either hematoxylin and eosin, modified Bielchowsky stain, and alkaline Congo red to visualize neurofibrillary tangles and senile plaques. Quantitative morphometric evaluation of neurofibrillary tangles and senile plaques were determined: using a micrometric scale for calibration readings were done with a 10 X objective for senile plaques and a 25X objective for neurofibrillary tangles. Diffuse plaques were excluded from all measurements. Screening of alkaline Congo red stains under polarized light was used to control for the reliability of tangle staining and, to a lesser extent, of the senile plaques' affinity for the modified Bielchowsky preparation. These criteria are consistent with those used in the classification of Khachaturian (Aubert I. et al., 1992, *J. Neurochem.*, 58:529–541).

II. Cholinergic Function in the Post-mortem Brain of Control and AD Subjects

Materials:

[$^3$H]QNB (45.7 Ci/mmol), [$^3$H]PZ (87.0 Ci/mmol), [$^3$h] AF-DX 116 (49.3, 57.0, or 70.0 Ci/mmol), [$^3$H]MCC (84.5 Ci/mmol), and [$^4$C]acetyl-CoA (48.8 mCi/mmol) are purchased from New England Nuclear (Boston, Mass., U.S.A.). Nicotine (free base), atropine sulfate, choline chloride, and eserine hemisulfate salts are bought from Sigma Chemical Co. (St. Louis, Mo., U.S.A.). ACh chloride was supplied by Hoffmann-LaRoche (Basel, Switzerland). Unlabelled acetyl-CoA are purchased from Boehringer Mannheim (Mannheim, F.R.G.). Tetraphenylboron (sodium salt) and 3-heptanone are purchased from Aldrich Chemical Co. (Milwaukee, Wis., U.S.A.). Ethyl acetate was bought from American Chemicals Co. (Montreal, Quebec, Canada). Bovine serum albumin (98% fatty acid free) and Ecolite scintillation cocktail are purchased from ICN Biochemicals (Irvine, Calif., U.S.A.). Triton™ X-100 (100%) scintillation grade was from Amersham (Arlington, Ill., U.S.A.). All other chemicals were from Fisher Scientific (Montreal, Quebec, Canada).

Human brain tissues

Are obtained at autopsy from individuals clinically diagnosed as having AD, PD, or PD/AD and from neurological normal age-matched controls. Tissues are provided by the Brain Bank of the Douglas Hospital Research Center (Y. Robitaille, neuropathologist). Histopathological criteria have been described earlier. Hemispheres to be used for biochemical assays are sectioned into thick (10 mm) coronal slices quickly and deeply frozen in 2-methylbutane at −40° C. before storage at −80° C. Before biochemical assays, brain slices are slowly thawed on a cold plate, and the following structures are dissected as follows: frontal (Brodmann areas 9 and 10) and temporal (Brodmann areas 20, 21, 22, and 38) cortices, hippocampus and cerebellum (use as a low pathology brain area).

Analysis of the results:

Binding parameters ($K_d$ and $B_{max}$ values) were derived from the saturation experiments analyzed by the computerized method LIGAND™ (Aubert I. et al., 1992, *J. Neurochem.*, 58:529–541). Statistical significance of differences between control and AD (0, 1, 2 copies of E4 alleles) brain was evaluated using Student's unpaired t test, with values of $p<0.05$ being considered significant.

Assay for Choline Acetyltransferase (ChAT) Activity:

Tissues from various brain regions were homogenized and incubated for 15 min. in buffer containing [$^{14}$C]acetyl-CoA as previously described in details (Aubert I. et al., 1992, *J. Neurochem.*, 58:529–541) to determine ChAT activity.

Multiple biochemical and anatomopathological studies have shown that the immunoreactivities and activities of cholinergic marker enzymes, such as ChAT, decrease in the neocortex as well as in the hippocampus of patients with AD. As shown in FIG. 6, the apoE4 allele copy number is inversely correlated with ChAT activity in the hippocampus and temporal cortex of age-matched control and AD subjects. In FIG. 6 each bar refers to mean value ±S.E.M.. Significant differences between groups are indicated by the number of stars: ★:p<0.05, ★★:p<0.01, ★★★<0.001. Striking reductions in ChAT activity were seen in apoE4 carriers. ChAT values are represented in FIG. 1 in the hippocampus (23 ADs and 30 controls) and temporal cortex (30 ADs and 12 controls) of AD subjects with different doses of apoE4 allele.

Statistical analyses indicate that ChAT levels in AD subjects (with 1 and 2 copies of apoE4) are significantly different from AD from control subjects (with 0 or 1 copy of apoE4).

Figure 7:
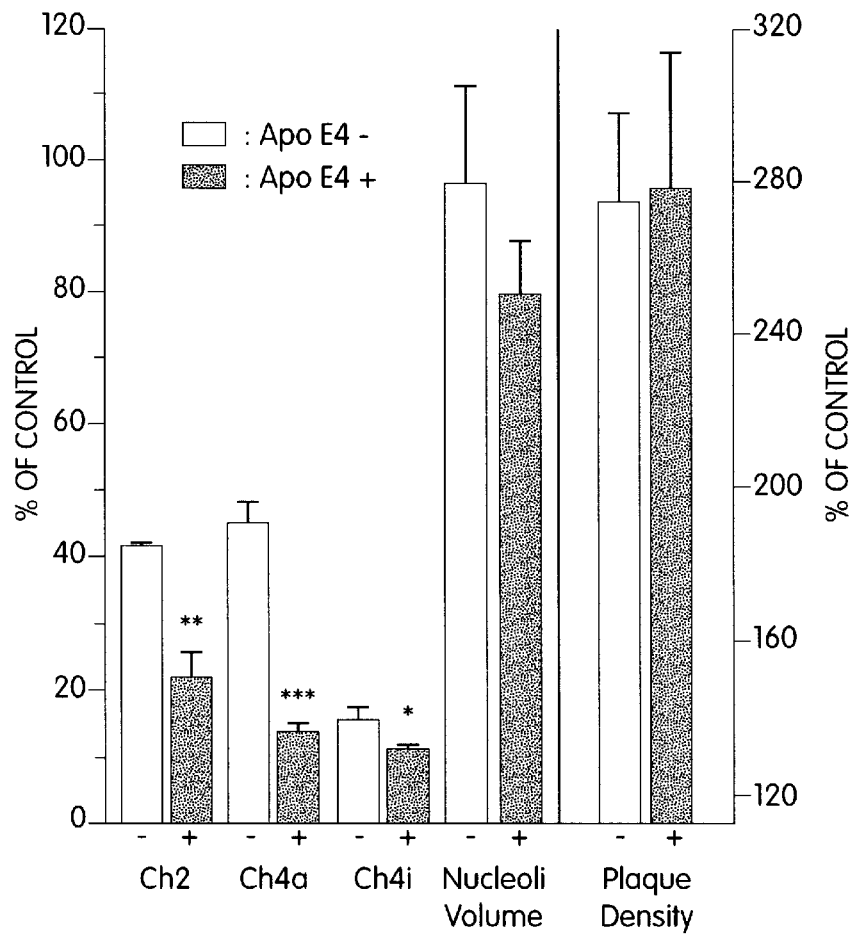
FIG. 7 illustrates the individual neuropathological and morphological characteristics associated to the cholinergic system in the brain of the various Alzheimer's disease and control cases investigated.

Acetylcholinesterase positive neuron density in the subcortical areas projecting to the temporal cortex and hippocampal structures are represented in FIG. 7. Neuronal cell density in the Ch2, Ch4*a* and Ch4*i* are expressed as percent of control values. Nucleolar volume is expressed in um$^2$. Plaque density is expressed as number per mm$^3$ in the hippocampus of the same patients. Portion of these results were published by Etienne and Colleagues (1986, *Neuroscience,* 19:1279–1291). The genotype of the original patients was unknown and could not be done then. Since then, we reanalysed the data in subjects for which genotype could be determined. Three AD subjects are apoE4 negative whereas four AD subjects are apoE4-positive. Results clearly confirm previous findings that AD subjects show marked loss of cholinergic neurons in Ch2, Ch4*a* and Ch4*i* but also highlight the fact that the present of the apoE4 allele potentiate significantly the loss of neurons in the Ch2 and Ch2*a* (p<0.01) and in the Ch4*i* (p<0.05).

Binding of [$^3$H]QNB to total populations of muscarinic sites:

Punches of cortical and subcortical tissues from control subjects and AD brains are homogenized, centrifuged, and resuspended in Krebs buffer as previously described in detail for [$^3$H]PZ assay. Final membrane pellets are suspended in buffer at a concentration approximating 3.0–5.0 mg of protein/ml. Aliquots of membrane-enriched homogenate (0.6–1.0 mg of protein) are incubated in Krebs buffer in the presence of a saturating concentration of [$^3$H]QNB (10 nM) for 60 min. at room temperature (23° C.) in a total volume of 0.5 ml. All assays are performed in duplicate. Bound [$^3$H]QNB is separated from free ligand by rapid filtration under reduced pressure through Schleicher & Schuell No. 32 glass filters, presoaked in 0.1% polyethylenimine solution, using a Brandel Cell Harvester apparatus (Brandel, Gaithersburg, Md., U.S.A.). Filters are then rapidly washed with ice-cold buffer, three times with 4.5 ml each, before being dried. The radioactivity of the filters is determined by liquid scintillation counting using a Beckman model LS7000 scintillation counter at 48% efficiency. Nonspecific binding, defined in the presence of 1 $\mu$M atropine sulfate, represents usually <15% of total binding.

Binding of [$^3$H]PZ to human brain muscarinic $M_1$ sites:

Brain tissues are processed as previously described earlier. Aliquots of final homogenates are incubated in Krebs buffer with various concentrations of [$^3$H]PZ (0.1–20 nM) for 60 min. at room temperature (23° C.). Assays are terminated and radioactivity is determined as described above for [$^3$H]QNB binding. Nonspecific binding, defined in the presence of total binding at ligand concentrations approximating $K_d$ values.

Binding of [$^3$H]AF-DX 116 to human brain muscarinic putative $M_2$ sites:

Brain tissues are processed as described above for [$^3$H] QNB. Aliquots of final homogenates are incubated in Krebs buffer with various concentrations of [$^3$H]AF-DX 116 (0.1–20 nM) for 60 min. at 4° C. Assays are terminated and radioactivity is determined as described above for [$^3$H]QNB binding. Nonspecific binding, defined in the presence of 1 $\mu$M atropine sulfate, represents usually <40% of total binding at ligand concentrations approximating $K_d$ values.

Muscarinic binding sites (total, M1 or M2) are not altered in the hippocampus of AD versus control subjects. The apoE genotype has no significant impact on the activity of these receptors. Muscarinic M1 and M2 receptor sites are not alters in AD versus control subjects in the temporal cortex whereas the so-called total (QNB) muscarinic binding sites are slightly reduced in AD versus control subjects (no genotype effect on this receptor group).

Bindinq of [$^3$H]MCC to human brain nicotinic sites:

Brain tissues are processed as described above for [$^3$H] QNB with the exception that samples were homogenized in 50 mM Tris-HCl buffer. Aliquots of final homogenates were incubated in 50 mM Tris-HCl buffer with various concentrations of [$^3$H]MCC (0.1–20 nM) for 60 min. at 4° C. Assays are terminated and radioactivity is determined as described above for [$^3$H]QNB binding. Nonspecific binding, defined in the presence of 10 µM nicotine, represents usually <50% of total binding at ligand concentrations approximating $K_d$ values.

Nicotinic Receptor Binding Sites are significantly reduced in apoE4 AD subjects whereas AD subjects not carrying apoE4 are not different from controls subjects. This is valid for both the hippocampal and the temporal areas in AD.

Analysis performed in our laboratory indicates that despite marked deafferentation and neuronal cell losses in the hippocampus of AD subjects, apoE protein levels remain unchanged or, decreased in apoE4 carrier subjects; this is consistent with our previous report using non-phenotyped AD subjects. The E4 allele is associated in periphery with abnormally low levels of apoE and high concentrations of circulating lipoproteins, increased amounts of plasma and LDL cholesterol, altered lipoprotein distribution and most importantly rapid catabolism of apoE4 compared to apoE3 (Gregg R. E. et al., 1986, *J. Clin. Invest.*, 87:815–821). This may suggest that apoE4 is metabolically different from apoE3 and could thus explain disturbances in lipid homeostasis reported in the AD brain. For example, phosphatidylcholine (PC), phosphatidylethanolamine (PE) and cholesterol levels are all significantly reduced in AD brains (Pettegrew J. W., 1989, *Ann. NY Acad. Sci.*, 568:5–28; Nitch RM et al., 1992, *Proc. Natl. Acad. Sci.*, 89:1671–1675) and have been shown to be inversely correlated with the number of senile plaques in cortical layers II and IV (Pettegrew J. W., 1989, *Ann. NY Acad. Sci.*, 568:5–28).

Brain membrane phospholipids, especially PC and PE, have been shown to play important roles in the availability of choline, a rate-limiting precursor of acetylcholine (ACh) (Nitch RM et al., 1992, *Proc. Natl. Acad. Sci.*, 89:1671–1675). The release from PC of free choline precursor for ACh synthesis is accomplished in a one step process through a phospholipase-D type enzyme in cholinergic neurons (Lee H. E. et al, 1993, *Proc. Natl. Acad. Aci. USA*, 90:10086–10090). Brain levels of choline are decreased by up to 40–50% in frontal and parietal cortices of AD patients (Nitch RM et al., 1992, *Proc. Natl. Acad. Sci.*, 89:1671–1675). Similarly, cholesterol is apparently required for the proper functioning of the nicotinic receptor (Jones O. T. & McNamee M. G., 1988, *Biochemistry*, 27:2364–2374). As losses of cholinergic neurons and/or ChAT activity are well known classical hallmarks of AD (Perry E. K. et al, 1977, *J. Neurol. Sci.*, 34:247–265; Davies P. et al, 1976, *Lancet*, 2:1403), a possible relationship between the apoE4 genotype and cholinergic deficits was deemed as highly relevant to investigate. We observed that reduction in ChAT activity in the hippocampus and temporal cortex of AD cases is inversely proportional to the apoE4 allele copy number (i.e. as apoE4 allele copy number increased, ChAT activity decreased). Our results thus clearly indicate the existence of distinct genetic entities in sporadic AD which show differential degrees of alterations of cholinergic innervation, at least as revealed by residual post-mortem ChAT activity. Another presynaptic marker of cholinergic projection, the nicotinic receptor, was also found to be markedly reduced in apoE4 AD subjects. Conversely, the typical post-synaptic marker, M1-muscarinic receptor was unaltered in AD versus control subjects, whether apoE4 is present or not. The M2-muscarinic receptor which represent a composite pre- and post-synaptic marker is also unaffected by the apoE4 allele gene dosage.

The correlation between apoE4 allele copy number and reductions in ChAT activity and nicotinic receptors may be explained by at least two distinct phenomena. First, phospholipids such as PC and PE, that can serve as precursors to choline in the synthesis of ACh, could be transported into neurons via the classical apoE-LDL receptor pathway (Goldstein J. L. et al, 1977, *Ann. Rev. Biochem.*, 46:897–930). An isoform-dependent impaired regulation of the transport of phospholipids in the brain of apoE4 carriers could explain the reduced levels of PC, PE and choline reported in AD (Pettegrew J. W., 1989, *Ann. NY Acad. Sci.*, 568:5–28; Nitch RM et al., 1992, *Proc. Natl. Acad. Sci.*, 89:1671–1675) which in turn could lead to decreased ACh synthetic capacities. This hypothesis is consistent with membrane defects reported in AD subjects such as changes in membrane fluidity in the hippocampus and platelets of AD patients. The loss of cholesterol reported in AD and the effect of apoE4 on nicotinic binding activity is very consistent with the apoE4/impaired lipid homeostasis hypothesis.

In addition, the reduction in neuronal ChAT activities and choline levels could parallel the loss of cholinergic neurons in the basal forebrain, including the nucleus basalis of Meynert (NBM), diagonal band of Broca (DBB) and the septal area. The analysis of the number of acetylcholinesterase-positive neurons in the NBM and DBB in genotypes AD patients revealed marked losses of cholinergic neurons in apoE4 carriers versus apoE3 homozygous AD cases.

EXAMPLE II

Acetylcholinesterase-Inhibitor (Tacrine, Parke-Davis) Treatment in Human with Alzheimer's Disease: Effect of ApoE Genotype.

Study design

The tacrine study results described here were originally published by Knapp, Gracon et al. (1994, *Journal American Medical Association*, 271:985–991), however, apoE genotypes were unknown in those days. The study was a 30-week study in which patients were randomized to one of four treatment groups: placebo or escalating doses of tacrine. In the tacrine treated group, all patients began treatment at 40 mg/day. One group had tacrine increased to 80 mg/day, on which they remained until the end of the study. The other two groups received tacrine in dosages escalated beyond 80 mg/days to 120 and 160 mg/day. Only the latter group of patients was considered in the present genotype analysis.

Forty Alzheimer disease patients who received the maximum dose of tacrine (40 mg/d for 6 weeks, 80 mg/d 6 weeks, 120 mg/d for 6 weeks 160 mg/d for 12 weeks for a total of 30 weeks) and completed the drug trial were selected to determine apoE phenotype using serum proteins as described before (Poirier et al., 1993, Apolipoprotein E phenotype and Alzheimer's Disease, *Lancet* 342:697–699). The patients selection was done on the basis of presence and absence of drug response to the treatment. The Alzheimer's Disease Assessment Scale (ADAS) was used to monitor treatment effects. Half of the selected patients showed drug responsiveness (positive ADAS differences) or lack of response (negative ADAS delta). We then examine the impact of different genotypes (apoE2/2, 3/2, 3/3, 3/4, 2/4 and 4/4) on therapeutic response using the ADAS-cog and the ADAS total test results obtained prior to and after tacrine administration. The ADAS-cog is an objective test that evaluates memory, attention, reasoning, orientation and praxis: a decrease score over time (or a positive difference) indicates improvement (Rosen W. G. et al, 1984, *Am. J. Psychiatr.,* 141:1356–1364). The ADAS total includes the cognitive and non-cognitive portion of the ADAS.

Figure 8A:
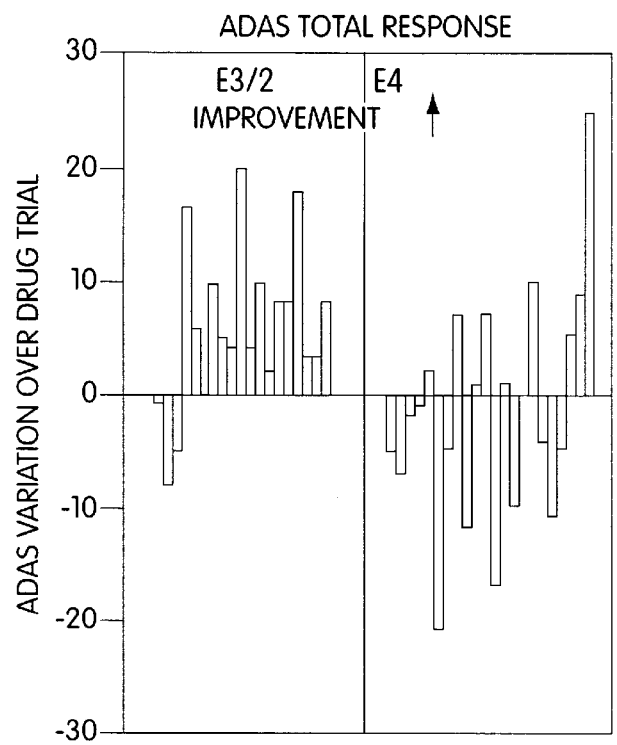
FIG. 8A–B illustrates the Alzheimer's disease assessment scale (ADAS) delta values (end values minus screen values) in tacrine-treated AD patients with different apoE genotype.
Figure 8B:
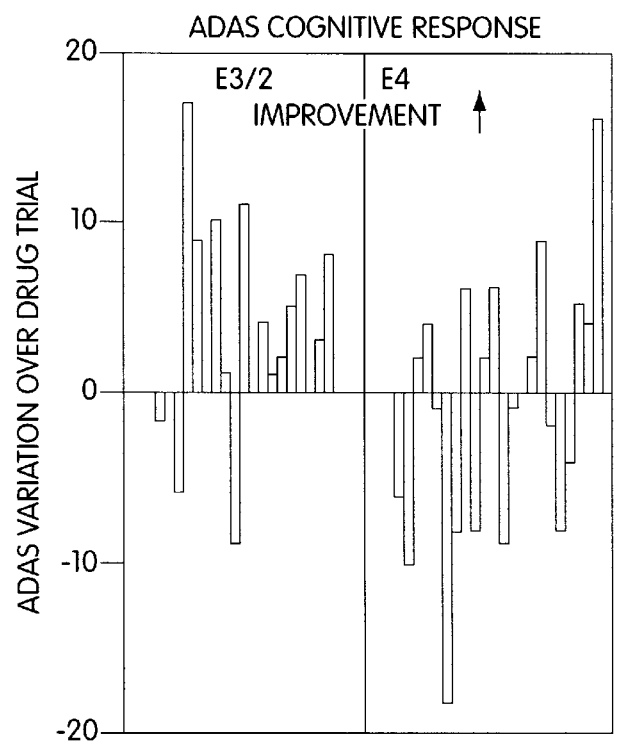

Cholinergic Drug Response in Genotyped AD Subjects:

FIG. 8 illustrates the drug responsiveness (ADAD-cog and ADAS total) of AD subjects as a function of apoE4 allele. Each bar represents an individual subjects. Positive delta values (difference in ADAS score at the end minus ADAS score prior to drug treatment) indicate improvement in cognitive performance (ADAS cog) and in global performances (ADAS-total). Negative values represent patients who deteriorated over time and drug treatment. All the subjects are AD subjects, all were treated with the same drug, at the same level, for the same duration. The only critical factor that differentiates them is the presence or absence of the apoE4 allele.

Result clearly indicates that more than 85% of the apoE4 negative subjects show improvement with tacrine administration (ADAS total) whereas 60% of the apoE4 positive subjects are worse following drug treatment. In other words, 4 out 5 subjects that do not response to tacrine are apoE4 positive. The ADAS-cog scale shows similar response profile in apoE4 carriers and non-carriers.

Taken together, our data clearly suggest that cholinergic function in AD-E3/3, 3/2 and 2/2 subjects are at least partially spared when compared to AD-E4/3, AD-E4/2 and AD-E4/4 carriers. Most importantly, this genetic susceptibility apparently results in subgroups of AD patients which respond differently to cholinomimetic-based therapies; with E4 carriers at a greater risk for loss of their ACh synthetic capacities. This hypothesis was formally tested in tacrine-treated AD subjects which showed different apoE genotypes. As expected, apoE4 negative subjects were found to respond tremendously well to the acetylcholinesterase inhibitor tacrine (an acetylcholine metabolism enhancer) when compared to apoE4 carriers.

The cholinergic hypothesis of geriatric memory dysfunction (Bartus R. T. et al., 1982, *Science,* 217:408–417) raises some fundamental questions regarding the observed heterogeneity of clinical responses toward various cholinomimetics in different AD patients. The absence of clear beneficial effects of choline and lecithin in geriatric patients with and without AD has always been quite perplexing. Furthermore, clinical trials based on the use of esterase inhibitors such as physostigmine (Davis K. L. et al, 1979, *N. Engl. J. Med.,* 301:946–951) and tacrine (Davis K. L. et al, 1992, *N. Engl. J. Med.* 327:1253–1259) have shown that contrary to young subjects, the optimal acute dose necessary to facilitate performance on memory tasks varied considerably among individual aged control subjects and AD patients.

The presence of the apoE4 allele appears now to be the most important factor responsible for individual variations in residual brain cholinergic innervation in AD and clearly predict clinical outcome of cholinergic based therapies. Clinical responsiveness to cholinergic agents monitored in genotyped AD patients demonstrated that apoE4 carriers are unlikely to be good responders, at least with the use of ACh precursors and esterase-based therapies.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A method for the identification of human subjects with cognitive impairments to be responsive to a cholinomimetic drug comprising determining the number of copies of apoE4 gene alleles in said subject and wherein the absence of at least one apoE4 gene allele indicates a predisposition to respond to a cholinomimetic drug.

2. A method of treating human subjects with cognitive impairments comprising identifying a subject according to the method of claim 1 and administering a therapeutically effective amount of a cholinomimetic drug wherein administration of the cholinomimetic drug improves cognitive performance.

3. The method of claim 2 wherein said cholinomimetic drug is selected from the group consisting of inhibitors of acetylcholine degradation, inducers of acetylcholine synthesis, acetylcholine agonists or mimics, and muscarinic M2-receptor antagonists.

4. The method of claim 1 wherein the number of copies of apoE4 gene alleles is determined indirectly by determining the presence of apoE2 and/or apoE3 gene alleles using appropriate apoE2 and apoE3 probes.

\* \* \* \* \*